United States Patent [19]

Pericic

[11] Patent Number: 5,290,302
[45] Date of Patent: Mar. 1, 1994

[54] SURGICAL INSTRUMENT

[75] Inventor: Ljubomir Pericic, Alphington, Australia

[73] Assignee: The University of Melbourne, Australia

[21] Appl. No.: 768,293

[22] PCT Filed: Apr. 6, 1990

[86] PCT No.: PCT/AU90/00135
§ 371 Date: Dec. 2, 1991
§ 102(e) Date: Dec. 2, 1991

[87] PCT Pub. No.: WO90/11723
PCT Pub. Date: Oct. 18, 1990

[30] Foreign Application Priority Data
Apr. 7, 1989 [AU] Australia ............... PJ3578

[51] Int. Cl.⁵ .................................. A61B 17/28
[52] U.S. Cl. ........................ 606/167; 606/170; 606/206
[58] Field of Search ............. 606/167, 170, 171, 205, 606/206, 208, 209; 128/753, 754, 755

[56] References Cited

U.S. PATENT DOCUMENTS

| | | | |
|---|---|---|---|
| 1,493,240 | 2/1923 | Bohn . | |
| 4,210,146 | 7/1980 | Banko | 606/171 |
| 4,258,716 | 3/1981 | Sutherland | 606/170 |
| 4,306,570 | 12/1981 | Matthews | 128/755 |
| 4,643,190 | 2/1987 | Heimberger | 606/205 |
| 4,760,848 | 8/1988 | Hasson | 606/206 |
| 4,770,174 | 10/1988 | Lackman et al. | 606/180 |
| 4,898,157 | 2/1990 | Messroghli et al. . | |

FOREIGN PATENT DOCUMENTS 8103122 11/1981 World Int. Prop. O. ........... 606/171

OTHER PUBLICATIONS

Grieshaber Switerzland, Augeninstrumente Ophthalmic Surgical Instruments Storz Ophthalmic Products, p. 98.
Dorc, Micro Surgical System ... p. 1286.
Spring Handle, p. 8.
New System of Intraocular Instruments, Arch Ophthalmol, vol. 101, May 1983.
Instruments for Introcular Microsurgery, Avd. Ophthal, vol. 37, 1978.
Surgical Mgmt. of ... Arch Ophthalmol, vol. 93, Oct. 1975.
Appliances A Non-Magnetic Foreign-Body Extractor, H. B. Stallard, Mar. 1950.
Diamond-Coated All-Purpose Foreign Body Forceps, Dyson Hickingbotham.

*Primary Examiner*—Edgar S. Burr
*Assistant Examiner*—John S. Hilten
*Attorney, Agent, or Firm*—Andrus, Sceales, Starke & Sawall

[57] ABSTRACT

A microsurgical instrument comprising a generally cylindrical handpiece (10) split longitudinally to provide two semi-cylindrical parts (12, 13) which are pivotally mounted at a first end thereof, to a central support member (14), for symmetrical pivotal movement at a second end towards and away from each other. A spring (26) biases the parts (12, 13) away from each other. A spindle (11) extends beyond the second end, comprising a pair co-axial shafts (16, 17) which are connected at the first end with respective levers (23, 24) to respective handpiece parts (12, 13) and at the second end to a functional tip of scissor, forceps, or the like, each jaw member of such a tip being connected to only one of the co-axial shafts (16, 17). Squeezing of the handpiece parts (12, 13) together causes simultaneous and symmetrical rotation of the co-axial shafts (16, 17) in opposite directions whereby the jaws of the functional tips are activated symmetrically and in unison.

3 Claims, 3 Drawing Sheets

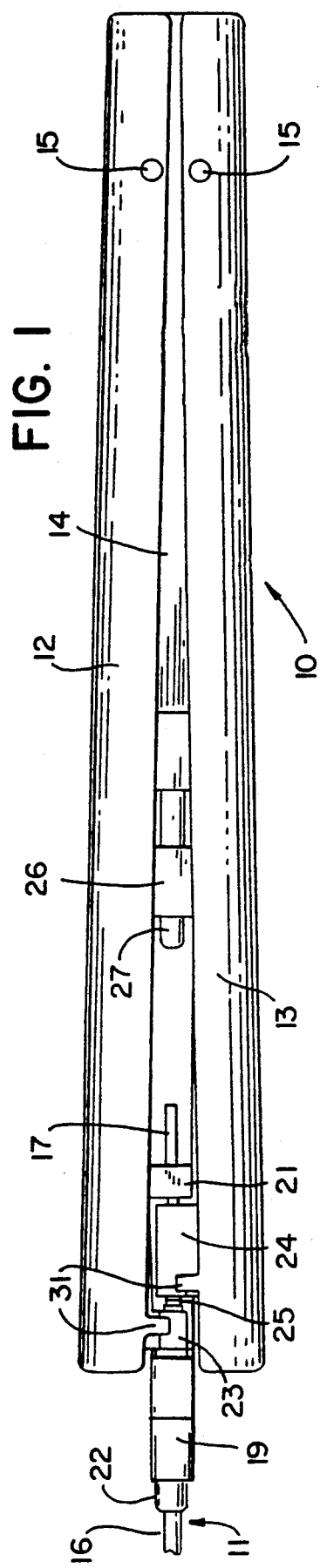
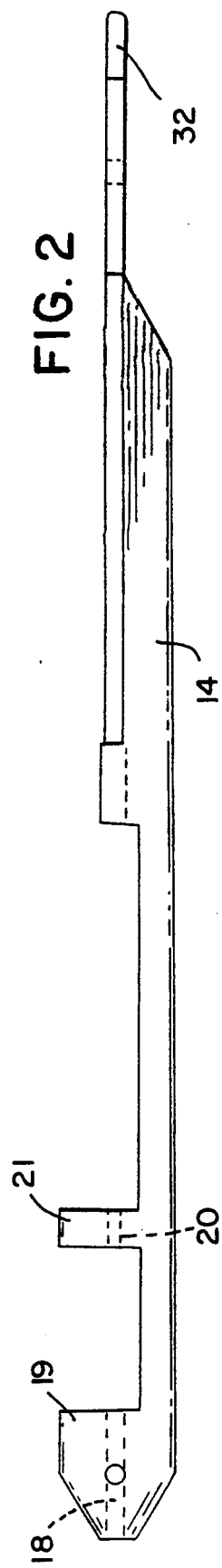
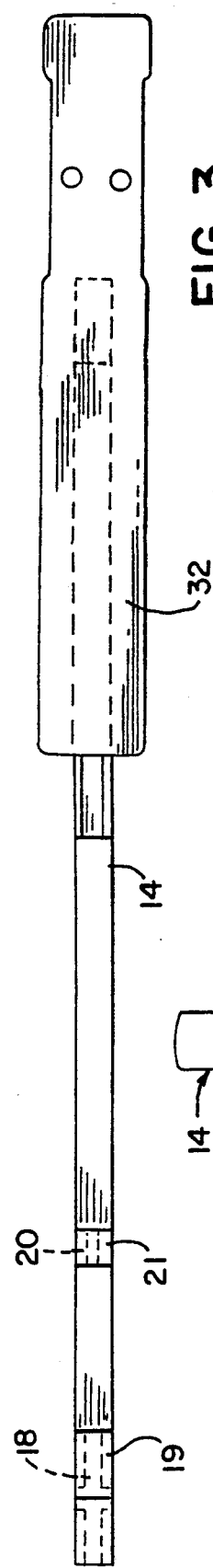

SURGICAL INSTRUMENT

The present invention relates to a surgical instrument and more particularly to an improved surgical instrument of the kind requiring actuation of a handpiece to cause movement of functional parts of the instrument which are mounted on a spindle and are thus remote from the handpiece. The invention is particularly concerned with such instruments as forceps, scissors and clamps of the kind used in performing micro surgical operations, for example, on the eye but of course any other type of surgical instrument having moving parts at the remote end thereof could incorporate the invention.

Surgical instruments in which actuation is achieved by squeezing parts of the instrument between the fingers of the surgeon have been developed and while they improve the ability of the surgeon to manipulate the rotational position of the end of the instrument while actuating the instrument, the drive mechanisms and pivotal arrangements of the actuating elements of the instruments have thus far not been altogether satisfactory.

For example, instruments wherein the spindle comprises co-axial shafts are known. In these the shafts are caused to slide axially relative to each other and a split-collett arrangement at the tip causes movement of the jaws. Whilst such an arrangement has the advantage that the jaws more symmetrically there is a problem in that intra ocular fluids enter the tip and cause binding of the mechanism due to corrosion if not cleaned away immediately after surgery. In addition protein could coagulate inside the mechanism and would eventually damage the working thereof if not cleaned away completely. The cleaning operation is complex and time-consuming if done properly and if not done properly the useful life of the instrument is severely curtailed.

One of the present applicant's earlier attempts to provide an improved surgical instrument of the kind in question involved co-axial shafts having relative rotary movement to cause operation of the jaws and whilst the rotary shafts overcame the problem of cleaning because there is no access for fluids into the spindle, only one of the jaws moves in this arrangement and this fact causes other problems for the surgeon. With only one jaw moving it is often the case that the surgeon, in the performance of a delicate operation, forgets which is the moving and which is the fixed jaw with the undesirable consequence that the material being cut or held may be moved transversely during an operation. consequently this earlier attempt was deemed unsatisfactory and was abandoned without publication.

It is an object of the present invention to provide an improved surgical instrument which avoids or overcomes one or more of the disadvantages of existing surgical instruments of the kind in question.

Accordingly the invention provides a surgical instrument including a handpiece comprising two parts connected for relative movement towards and away from each other, a spindle extending from said handpiece to a functional tip comprising jaw members at an end of the spindle remote from said handpiece, said spindle comprising coaxial shafts each connected to a respective handpiece part and a respective jaw member whereby said relative movement of the handpiece parts causes, via said shafts, relative movement of said jaw members towards or away from each other, characterized in that, said handpiece is of generally cylindrical configuration split longitudinally to provide said two parts which are connected, towards one end thereof, for symmetrical pivotal movement towards each other under pressure from the user and away from each other under internal bias whereby said symmetrical movement of the handpiece parts causes symmetrical movement of said jaw members by causing rotation of said shafts in opposite directions.

In order that the invention may be more readily understood one particular embodiment will now be described in detail with reference to the accompanying drawings wherein:

FIG. 1 is a side elevation of a surgical instrument according to the invention with jaw members excluded;

FIG. 2 is an underside view of an axial support member of the instrument of FIG. 1;

FIG. 3 is a side view of the support member of FIG. 2;

FIG. 4 is an end view of the support member of FIG. 2;

Figure 14A:
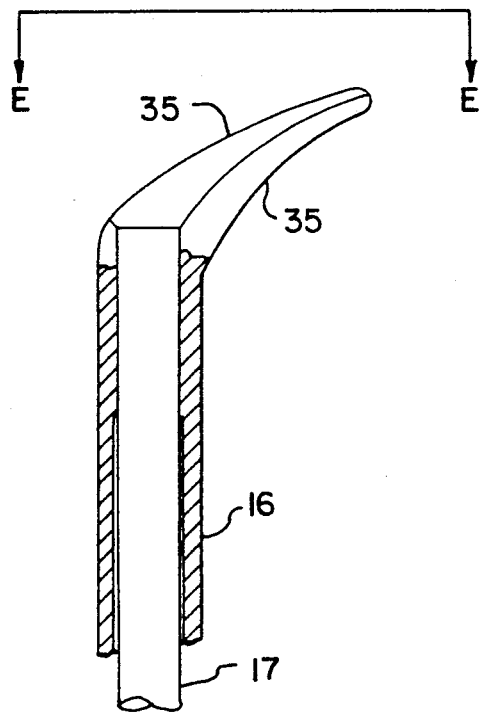
FIG. 14A shows a partially cut away side view of jaw members forming a portion of the instrument.
Figure 14B:
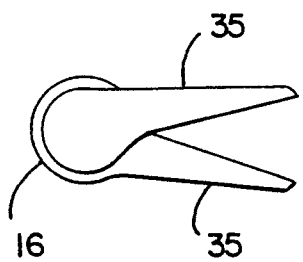
FIG. 14B in a view taken along the line E—E of FIG. 14A.

The surgical instrument is shown to comprise generally a handpiece 10 of generally tapered cylindrical configuration and having extending from one end thereof coaxially with the axis of the handpiece 10 a spindle 11 which extends to jaw members 35 shown in FIG. 14 which in this case constitute surgical scissors. The handpiece 10 consists essentially of two semi-cylindrical hollow handgrip members 12 and 13 respectively. The handgrip members 12 and 13 are pivotally mounted adjacent one end thereof to a central support member 14. The handgrip members are connected to the central support 14 by respective pins 15.

The shape of the central support member 14 is more evident in FIGS. 2, 3 and 4 and it has a number of protrusions which provide support for the various components of the instrument as will be evident hereinbelow. The spindle 11 comprises an outer shaft 16 and an inner shaft 17 which is rotatably inserted in an axial bore of the outer shaft 16. The inner shaft 17 extends into the handpiece 10 beyond the inner end of the outer shaft 16 as is evident in FIG. 1. The spindle 11 is supported in the central support member 14 by passing through bore 18 in boss 19 and the inner shaft 17 also passes through bore 20 in boss 21. A stop member 22 is formed on the outer shaft 16 and bears against the end of the boss 19.

A first lever member 23 is mounted on the outer shaft 16 and a second lever member 24 is mounted on the inner shaft 17. The lever members 23 and 24 are fixed to the respective shafts. A spring 25 acts between the first and second lever members 23 and 24 to force them apart whereby pressure is maintained on the jaw member 35 constituting the respective jaws of surgical scissors attached to the end of the spindle 11. The jaw members are attached to the inner and outer shafts 16 and 17 respectively whereby rotation of the shafts in opposite directions causes the jaw members to open and close in a scissors type action. The spring 25 comprises 10 turns of standard round wire permacrome of 0.2 mm diameter (Cat. No. 211-080) Unitek Corporation, Monrovia, Calif. 91016. In the case of a surgical instrument in the form of forceps the spring 25 is omitted since it is not necessary to maintain a force between the jaw members as is the case with surgical scissors. As mentioned above, the handgrip members 12 and 13 are pivotally attached to the central support member 14 by pins 15.

Figure 10:
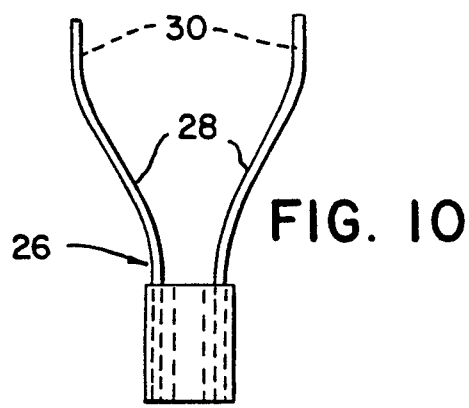
FIG. 10 is a plan view of a spring member of the instrument.
Figure 11:
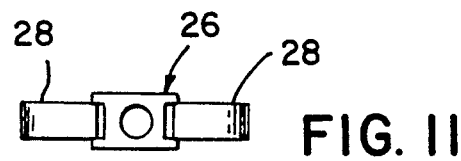
FIG. 11 is an end view of the spring of FIG. 10.
Figure 12:
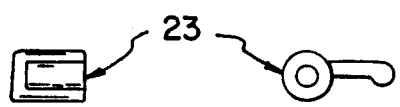
FIGS. 12 and 13 show elevations and end views of respective lever members of the instrument.
Figure 13:
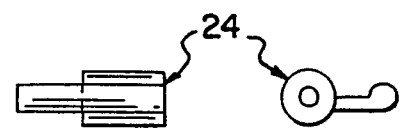

In order to bias the handgrip members apart as shown in FIG. 1, a spring member 26 is provided on shaft 27 which fixes the spring member 26 to the central support member 14. The spring member 26 has opposite arms 28 which bear against the inside surface of the respective handgrip members 12 and 13 and are positively located in position by respective pins 29 which pass through apertures 30 in the ends of the respective arms 28. The spring member 26 is more clearly shown in FIGS. 10 and 11.

Figure 5:
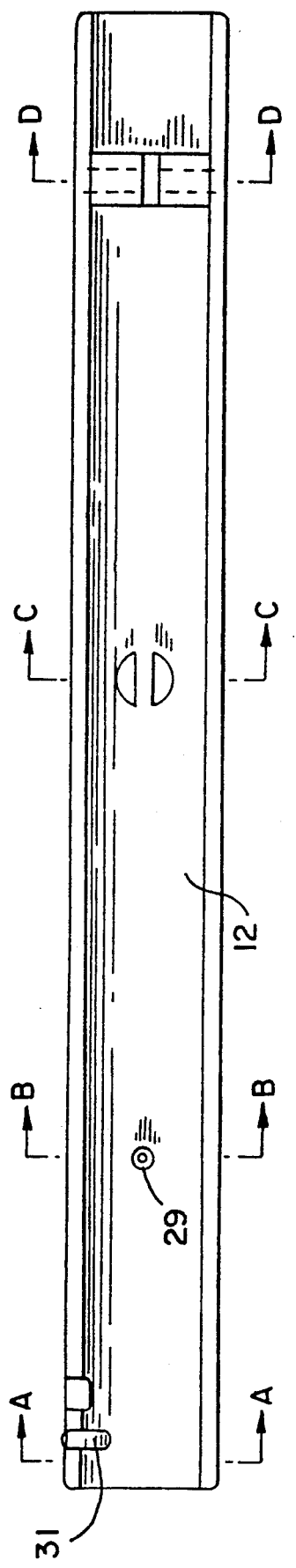
FIG. 5 is a view from inside of one of two semi-cylindrical side members of the instrument according to FIG. 1.
Figure 9:
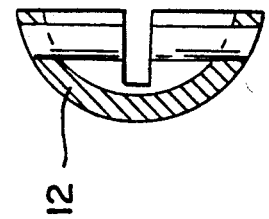
FIGS. 6–9 are sections on the lines A—A to D—D respectively of FIG. 5.
Figure 8:
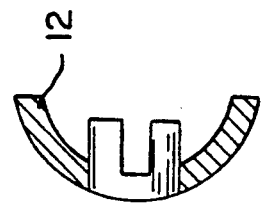
Figure 7:
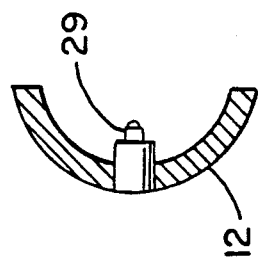
Figure 6:
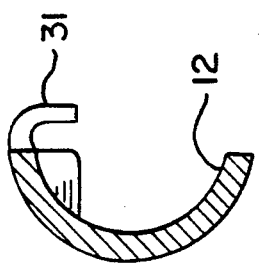

In FIG. 6 there is shown one of the handgrip members 12 with U-shaped engagement member 31 for engaging with the first lever member 23 for the purpose of rotating the outer shaft 16. A similar engagement member is fixed to the other of the handgrip members 12 for the purpose of actuating the second lever member 24 to rotate the inner shaft 17. As will be evident, when the surgeon squeezes the handgrip members 12 they move towards each other symmetrically and thereby, via engagement members 31 and respective lever members 23 and 24 rotate the outer and inner shafts 16 and 17 respectively in opposite directions. This causes symmetrical actuation of the jaw members 35. It should be further evident that by having coaxial rotational shafts, it is possible to fit the inner shaft 17 within the outer shaft 16 with minimal clearance whereby rotation is readily effected without allowing the pasage of any fluids within the clearance space between the two shafts.

The components of the surgical instrument are formed of stainless steel grade 316 and the various parts are joined where appropriate by being silver brazed together. Any dimensions shown in the drawings are in millimeters. It will be further evident that pivotal movement of the handgrip members 12 and 13 away from each other is restricted by the ends of the respective members at the pivotal end beyond the pivoting point, bearing on an end stop 32 formed as part of the central support member 14.

It should be noted that the present invention as described herein provides an improved surgical instrument which has considerable advantages over prior art instruments known to the applicant. For example, the cylindrical shape of the handpiece 10 allows the surgeon to readily rotate the handpiece between the fingers in the event that it is necessary to rotate the jaw members during the performance of an operation. Furthermore, the symmetrical movement of the handgrip members 12 as well as the symmetrical movement of the jaw members 35 minimizes or abolishes movement of the instrument away from the central longitudinal axis of the instrument during operation. In other words, as opposed to an instrument where only one part or side of the handpiece and one of the jaw members moves, while the other is stationary, the present instrument is unique and much more easily controlled. The fact that the cutting or gripping action of the jaw members reproduces the action of the fingers in compressing the handgrip members together simplifies use of the device and gives the surgeon a much more precise "feel" of the action which is being performed. This is contrary to the known collett type instruments which involve a linear movement to the shafts by way of coaxial sliding action to cause opening and closing of the jaw members. In addition, the precise interfitting of the coaxial shafts and the arrangement of jaw members thereon eliminates an internal cavity which is accessible by intraocular fluids and therefore the need for complicated and time-consuming cleaning internally of the spindle 11 is avoided. The equal and simultaneous movement of both the jaw members and the handgrip members allows the instrument to be precisely positioned and held in a very steady position during use. This symmetrical movement minimizes disturbance from the central longitudinal axis which greatly improves control during use of the instrument.

As will be evident the jaw members can be varied to provide differing surgical instruments such as forceps, scissor and clamps and it is conceivable that other types of jaw members may also be utilized.

We claim:

1. A surgical instrument, comprising:
   a tapered, generally cylindrical elongated handpiece (10) having a longitidinal axis, and having a narrower first end and a wider second end, said handpiece being split along the direction of elongation to form two elongated parts (12, 13), said handpiece parts being of hollow, generally semi-cylindrical configuration and being connected at said narrower first end for relative symmetrical pivotal movement toward each other under pressure from a user of the instrument and away from each other responsive to a bias spring provided in said handpiece;
   a functional tip comprising a pair of jaw members each of which is symmetrically moveable toward and away from the other jaw member;
   a spindle extending from said second end of said handpiece to said functional tip and having a longitudinal axis that is coaxial with said handpiece longitudinal axis, said spindle comprising rotatable coaxial shafts (16, 17) each of which is connected to a respective jaw member;
   a longitudinally extending support member (14) extending centrally along the length of said handpiece, wherein said handpiece parts are each pivotally connected to said support member adjacent said first end, and wherein said coaxial shafts are rotationally mounted on said support member at said second end of said handpiece; and
   means connecting each of said handpiece parts to one of said coaxial shafts for converting the relative, symmetrical movement of the handpiece parts toward and away from each other to rotation of each of said shafts in opposite directions relative to each other for causing said symmetrical movement of said jaw members, said connecting means including
      first (23) and second (24) levers coupled between said handpiece parts and said coaxial shafts, each lever cooperating with respective ones of said handpiece parts and shafts to cause rotational movement of the respective shaft upon movement of the handpiece part.

2. A surgical instrument as defined in claim 1 wherein said instrument is a micro-surgical scissors instrument, characterized in that said first and second levers are axially arranged with respect to said coaxial shafts, and wherein a compression spring (25) is provided between said levers to bias said levers axially apart so as to maintain a mating force between the respective jaw members so as to provide a scissors type action.

3. A surgical instrument as defined in claim 1, characterized in that each of said levers includes a forked engagement member (31) in the respective handpiece part.

* * * * *